United States Patent
Boyd et al.

(10) Patent No.: US 6,402,040 B1
(45) Date of Patent: Jun. 11, 2002

(54) TICKET AND METHOD OF METERING THE USE OF A FACILITY

(75) Inventors: Melissa D. Boyd, Corvallis; Paul H. McClelland, Monmouth; Marshall Field, Corvallis, all of OR (US)

(73) Assignee: Hewlett-Packard Company, Palo Alto, CA (US)

( * ) Notice: Subject to any disclaimer, the term of this patent is extended or adjusted under 35 U.S.C. 154(b) by 0 days.

(21) Appl. No.: 09/745,602

(22) Filed: Dec. 22, 2000

(51) Int. Cl.[7] .............................................. G06K 19/06
(52) U.S. Cl. ........................ 235/492; 235/487; 235/380; 235/382
(58) Field of Search ................................. 235/375, 380, 235/382, 382.5, 381, 386, 487, 488, 489, 491

(56) References Cited

U.S. PATENT DOCUMENTS

| | | | |
|---|---|---|---|
| 3,648,838 A | * 3/1972 | Hiromura | ................ 209/74 M |
| 3,653,587 A | * 4/1972 | Hammond et al. | ....... 235/50 R |
| 5,565,148 A | 10/1996 | Pendergrass, Jr. | |
| 5,949,522 A | 9/1999 | Manne | |
| 6,024,783 A | 2/2000 | Budman | |
| 6,025,902 A | 2/2000 | Wittek | |
| 6,090,192 A | * 7/2000 | Torii et al. | ................ 106/31.18 |

FOREIGN PATENT DOCUMENTS

| | | |
|---|---|---|
| WO | WO 00/15268 | 3/2000 |
| WO | WO 00/15269 | 3/2000 |

* cited by examiner

*Primary Examiner*—Karl D. Frech (57) ABSTRACT

A ticket including a base member, a discolorable member carried by the base member, and a discoloration system carried by the base member. The discoloration system is initially configured such that the discoloration system selectively discolors a first predetermined portion of the discolorable member in response to the application of a first energy pulse without discoloring a second predetermined portion of the discolorable member. The discoloration system is also adapted to be reconfigured by the first energy pulse such that the second predetermined portion of the discolorable member will be discolored in response to the application of a second energy pulse.

35 Claims, 5 Drawing Sheets

TICKET AND METHOD OF METERING THE USE OF A FACILITY

BACKGROUND OF THE INVENTIONS

Consumers today are able to chose from a wide variety of devices, events and facilities that provide acoustic and/or visual stimulation (collectively herein "acoustic/visual stimulators"). Other facilities and forms of recreational activity, such as skiing and amusement parks, are also available.

Referring first to acoustic/visual stimulators, current acoustic/visual stimulators include, but are not limited to, electronic devices such as computer, hand-held device or console-based video games and educational programs, cinemas, televisions, compact disk and audio cassette players, digital video disk and video cassette players, electronic books, and MP3 players, while new electronic devices are introduced all of the time. Live theater, concerts and museums are other types of acoustic/visual stimulators.

In recent years, there have been many attempts to increase the level of stimulation provided by acoustic/visual stimulators beyond mere acoustic and visual stimulation. Virtual reality rides, where riders are placed within a compartment that moves in concert with the acoustic and visual stimulation, are one example of such attempts to augment conventional acoustic/visual stimulators.

Another way to increase the level of stimulation provided by acoustic/visual stimulators is to deliver scents that correspond to the acoustic and visual stimulation. Currently proposed scent delivery systems involve the use of a device that houses scent materials and delivers the scents as appropriate. A base set of scent "primitives" are stored and mixed as needed by the systems to generate the desired scent. The inventors herein have determined that there are a number of factors inhibiting the economical commercial development of these systems. For example, the development of accurate scent primitives and a scent description language that can be used by a storage and mixing apparatus to accurately produce scents is likely to be quite expensive, as is development of the storage and mixing apparatus itself.

Turning to other forms of recreational activity, many of these activities require the use of tickets and other devices which meter participation (all such devices are referred to herein as a "ticket" for simplicity). Tickets are also used for buses, movies and the like. Many tickets are intended to allow the user to participate in a particular activity a number of times. At ski lifts, for example, a lift ticket will typically be configured such that it can be "punched" each time the user rides the ski lift. The inventors herein have determined that conventional tickets, as well as the conventional methods of "punching" the tickets, are susceptible to improvement.

SUMMARY OF THE INVENTIONS

Accordingly, one object of the present inventions is to provide apparatus that avoids, for practical purposes, the aforementioned problems in the art. In particular, one object of the present inventions is to provide a scent storage device that will be convenient, easy to use, accurate and inexpensive. Another object of the present inventions is to provide a device that may be used to, for example, selectively activate predetermined portions of a scent material supply. Still another object of the present inventions is to provide improved tickets and ticket punching methods.

In order to accomplish some of these and other objectives, a scent storage device in accordance with one embodiment of a present invention includes a base member and a plurality of scent channels carried by the base member. Each scent channel include a scent material supply and a scent activation system that selectively activates predetermined portions of the scent material supply. The scent material in each of the channels may, for example, produce a different scent.

The present scent storage device has a wide variety of applications. One application is in combination with an acoustic/visual stimulator such as a computer based video game. Here, the scent storage device would be relatively small (i.e. about the size of trading card so that it could be easily packaged with the game software) and store a variety of different pre-mixed scent materials in the respective scent channels. The scents produced by the scent materials correspond to events that take place during the game. The scent storage device may be connected to a scent delivery device that will cause the scent activation system for each channel to active the scent material in that channel as appropriate. For example, one of the channels may store a smoke scent. When an explosion occurs in the game, the computer will instruct the scent delivery device to cause the activation system with the smoke scent supply channel to activate a portion of the scent material supply and release the scent material.

Given its relatively small size, the aforementioned embodiment of the present scent storage device advantageously allows it to be easily carried by the user. Thus, it may be handed out to patrons as they enter movie theaters, live theaters, concerts, museums or virtual reality rides. They may then simply carry their scent storage device to their seat or to an particular exhibit and insert it into an appropriate delivery device. The present scent storage device may also be given away as a promotional item for advertising purposes.

In addition to its portability, the present scent storage device also provides a number of advantages over the currently proposed scent delivery systems. For example, the present storage device is simple, self-contained and relatively inexpensive. It does not require the development of scent primitives, a device to mix them, and scent description language to control the mixing process, as do the currently proposed systems. Additionally, because the scents are pre-defined and the scent material stored in its final state, the present scent storage device allows the scents to be perfected prior to manufacturing, as opposed to having to be mixed on the fly from scent primitives, as in the currently proposed systems.

In order to accomplish some of these and other objectives, a ticket in accordance with a preferred embodiment of a present invention includes a discolorable member and a discoloration system carried by the base member, initially configured such that the discoloration system selectively discolors a first predetermined portion of the discolorable member in response to the application of a first energy pulse without discoloring a second predetermined portion of the discolorable member.

Such a ticket may be "punched" by, for example, simply inserting the ticket into a device that provides an energy pulse. The resulting discoloration will provide visual feedback that is particularly useful in, for example, measured fare applications such as tickets for buses, ski lifts and amusement parks. Both the consumer and the operator will be able to readily determine how many fares, lifts or amusement rides remain on the ticket by simply reviewing the ticket.

In order to accomplish some of these and other objectives, a resistor array in accordance with one embodiment of a present invention includes a series of spaced first conductor members, a series of initially substantially non-conductive switches connecting adjacent first conductor members to one another, a second conductor member, and a series of resistors extending from respective first conductive members to the second conductor member. In one embodiment, the resistors may be configured such that they will burn out and disconnect from the second conductor member in response to the application of a predetermined short power pulse. The heat generated by the resistor will also cause the switch to become conductive so that the next conductor and resistor in the series will be connected to the pulse source. However, because the predetermined power pulse is short, the pulse will have passed before the next conductor and resistor is connected. The next resistor will not be consumed until the next power pulse.

There are a wide variety of uses for such a resistor array. One such use is associated with the aforementioned scent storage device, where the array may be used to selectively activate predetermined portions of a scent material supply formed from a solid material, such as wax, and a scent material. Heat from a resistor will melt the wax in the portion of the scent material associated with the resistor and release the scent material. Other uses include tickets and counters. Here, heat from the resistors may be used to create visual feedback, such as the discoloration of predetermined portions of the ticket, which indicates how may times the ticket has been "punched."

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions. For example, scent storage and delivery devices in accordance with the present inventions may be used in combination with any acoustic/visual stimulator. Thus, although the exemplary storage and delivery devices are described in the context of a computer based stimulator, the inventions are not so limited. Additionally, certain aspects of the scent storage devices are inventive in and of themselves and have application in other areas. One example is the passive sequential resistor array described below.

Figure 1:
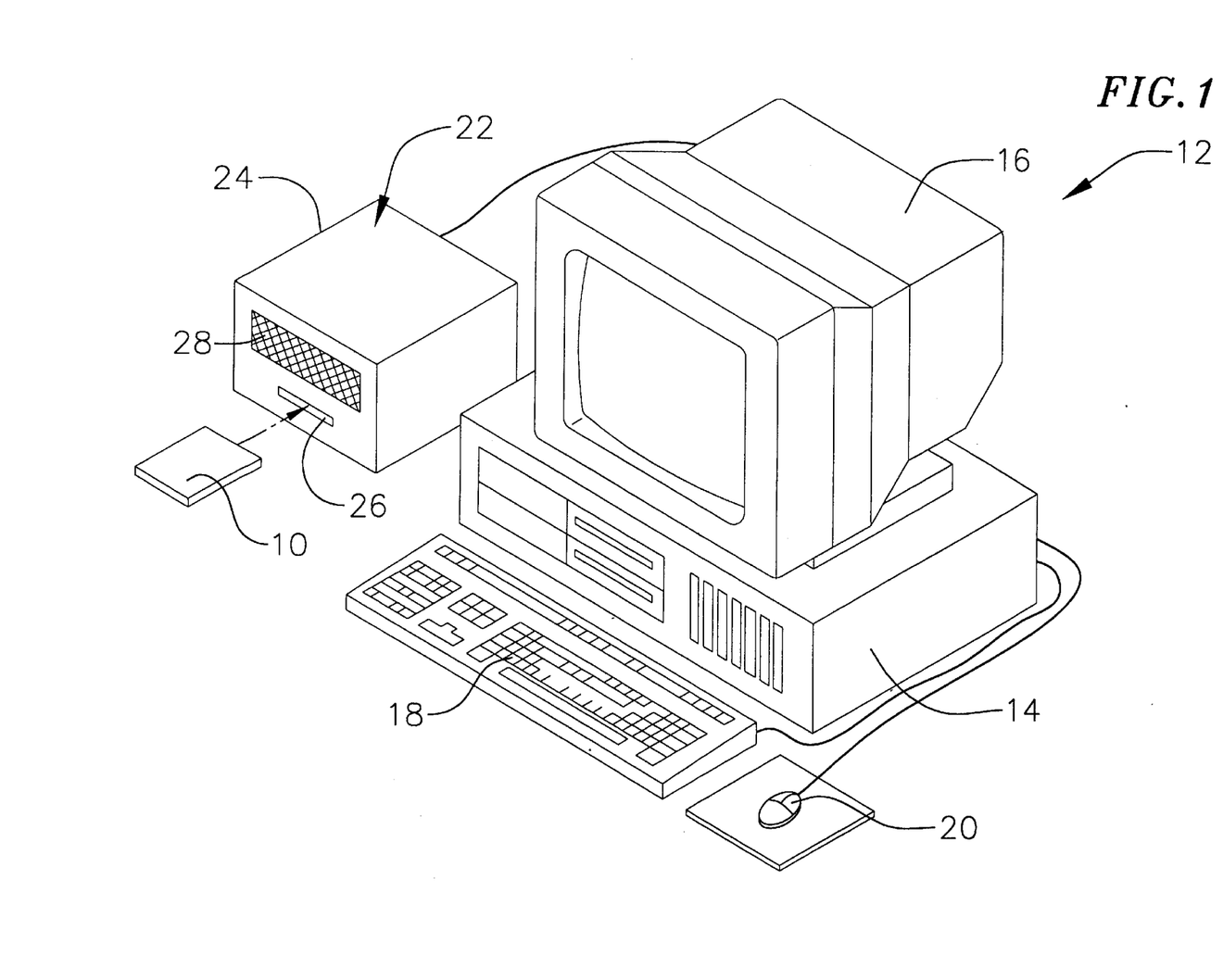
FIG. 1 is a front view of a computer system with a scent delivery device in accordance with a preferred embodiment of a present invention.

As illustrated for example in FIG. 1, a scent storage device 10 in accordance with one embodiment of a present invention may be used in conjunction with a computer system 12 that includes a processing unit 14, a monitor 16, a keyboard 18 and a mouse 20. The computer system 12 is also provided with a scent delivery device 22 having housing 24, a slot 26 which allows the scent storage device 10 to be inserted into the housing, and a screened outlet 28 through which the scents are emitted. Additional details concerning the exemplary scent delivery device are provided below with reference to FIGS. 6 and 7.

Figures 2, 3:
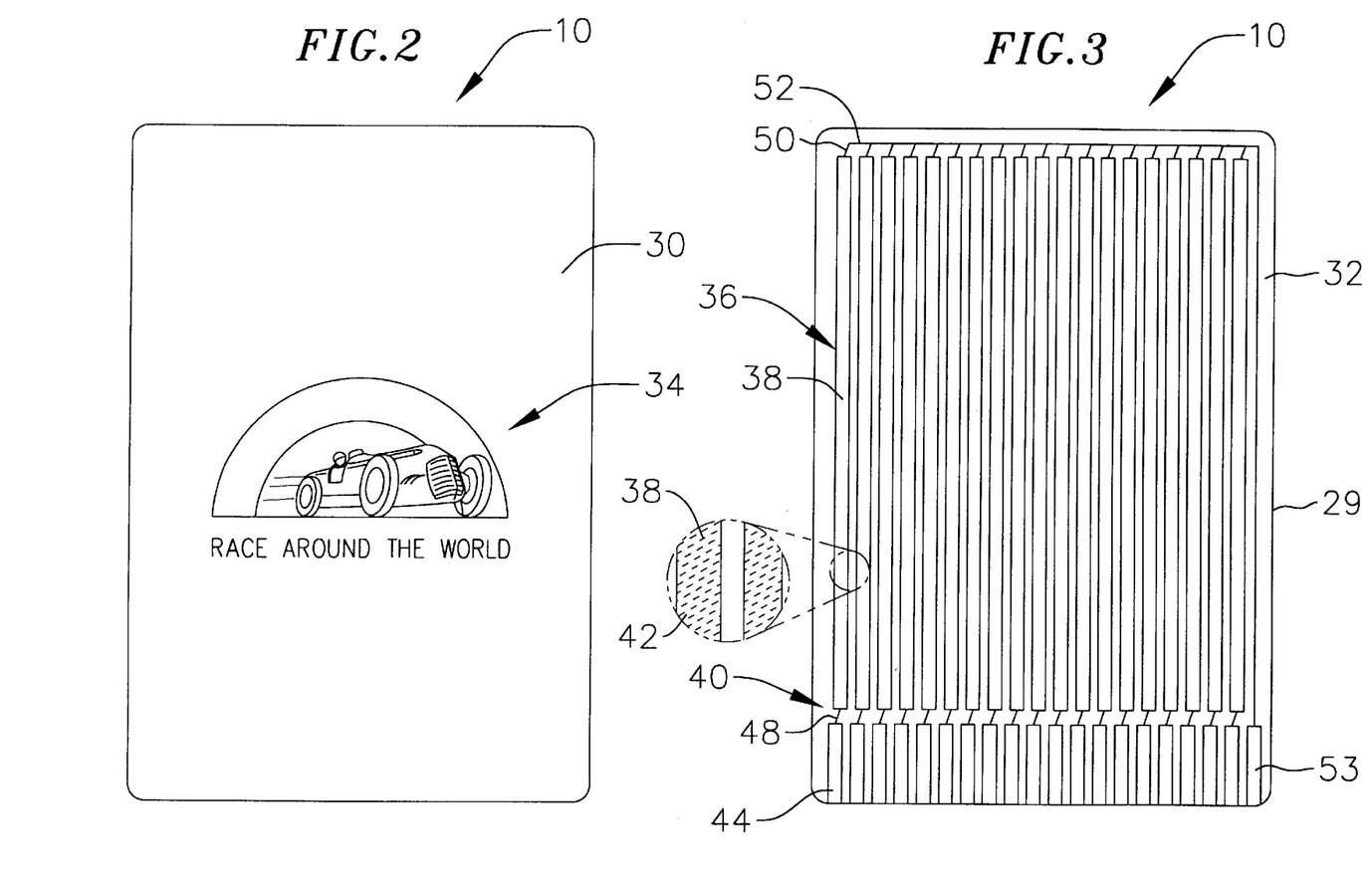
FIG. 2 is a front view of a scent storage device in accordance with a preferred embodiment of a present invention.
FIG. 3 is a rear view of the exemplary scent storage device illustrated in FIG. 2.

Turning to FIGS. 2 and 3, the exemplary scent storage device 10 is in the form of a trading card-sized device (approximately 3⅜ inches long×2⅛ inches wide) that may be readily held in the user's hand including a base 29 with a front side 30 and a rear side 32. Of course, depending on application, the length may range from ½ inch to 6 inches and the width may range from ½ inch to 6 inches. Suitable materials for the base include polyester and polyimide with thicknesses ranging from 0.014 inch to ¼ inch. The size, material and thickness selection will, of course, depend on the intended application. Identifying indicia 34 or other material may be printed on the front side 30. The rear side supports a plurality of scent channels 36 that produce scent events when activated. There are nineteen scent channels 36 in the exemplary embodiment and each of the scent channels may be used to produce a different scent. Alternatively, some of the scent channels 36 may produce the same scent or, if the application so requires, all of the channels could produce the same scent. The number of scent channels may, of course, be adjusted as desired or as applications and size constraints so require. A single scent channel 36 may also be used to produce different scents over the length of the channel. To that end, the scent channels may have a continuous configuration, as shown in the illustrated embodiment, or may consist of a series of dots or other discrete structures.

The scents preferably correspond to the acoustic/visual stimulation that the user will be receiving from the acoustic/visual stimulator at the time of the scent event. In the illustrated embodiment, the scent storage device 10 is intended for used with an educational video game entitled "Race Around The World" in which the participants race through various places throughout the world and the stored scents are associated with those places. [To the inventors' knowledge, no such game exists and the game concept is merely being used to illustrate certain aspects of the present inventions.] For example, one of the channels may be used to produce the scent of gumbo and this scent would be produced when the participants are racing through the streets of New Orleans. Another channel could be used to produce the scent of pine trees when the race enters the pine forests of northern Arizona.

Referring more specifically to FIG. 3, the exemplary scent channels 36 each include a scent material supply 38 and a scent activation system 40. The scent material supply 38 includes at least one, and preferably many, individual event portions 42 and the activation system selectively activates and consumes individual event portions 42. [The dashed lines between the event portions 42 have been added merely to illustrated the boundaries between the event portions and do not represent actual structural elements.] The scent channels 36 in the illustrated embodiment, for example, include approximately seventy individual event portions 42. The scent material supply 38 in each scent channel 36 preferably consists of scent material that is suspended in an odor-free solid material that will vaporize at moderate temperatures (i.e. 50° C. to 200° C.). Wax is one example of such a solid material. Other materials include glycols, ethers and gelatins. Examples of suitable scent materials include volatile oils such as terpinol. Additional information concerning scent material supplies may be found in U.S. Pat. No. 5,051,305.

The exemplary scent activation systems 40, which may be electrically connected to the scent delivery device 22 by contacts 44, preferably include of a series of resistors—one resistor for each event portion 42—in a passive sequential resistor array. For each scent event, a relatively short power pulse is supplied to the appropriate scent channel 36 by the scent delivery device 22. As discussed in detail below, the pulse will cause the first resistor in the series to heat up and vaporize the solid material in the associated event portion 42, thereby releasing the scent material. The pulse also causes the resistor itself to vaporize, thereby disconnecting that event portion 42 from the circuit, and causes the next resistor in the series (and, accordingly, the next event portion) to be connected to the circuit. This process will be able to continue for any of the scent channels 36, one scent event and one event portion 42 at a time, until that scent channel runs out of event portions.

Figure 4A:
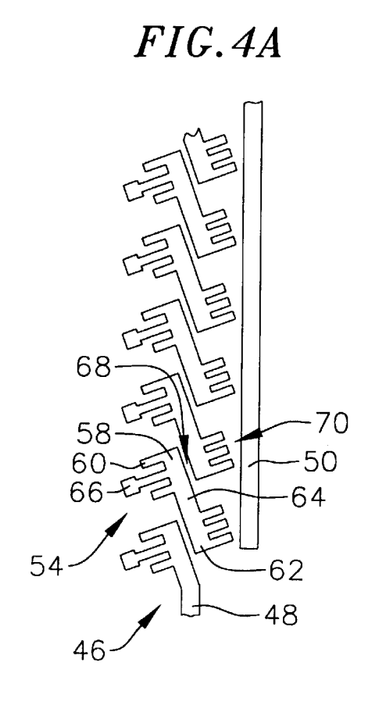
FIG. 4A is a partial plan view showing a portion of a scent channel from the exemplary scent storage device illustrated in FIGS. 2 and 3.

FIGS. 3 and 4A–4E illustrate an exemplary scent channel 36 during various stages of its construction. Referring first to FIGS. 3 and 4A, the exemplary scent activation systems 40 include a first conductor 46, which is connected to one of the contacts 44 at its forward end 48, and a second conductor 50, which is connected to a return line 52. A return contact 53, which is grounded by the delivery device 22, is connected to the end of the return line 52. As illustrated for example in FIGS. 4A and 4B, the first conductor 46 consists of a series of discrete conductor members 54 and a series of switching elements 56. The exemplary conductor members 54 each include a first connector portion 58 with extensions 60, a second connector portion 62 with similar extensions, and an intermediate section 64 extending between the first and second connector portions. Note, however, that the first conductor member 54 in the series only includes a first connector portion 58 and a linear portion that forms the forward end 48. The conductor members 54 also include a resistor contact 66.

Figure 4B:
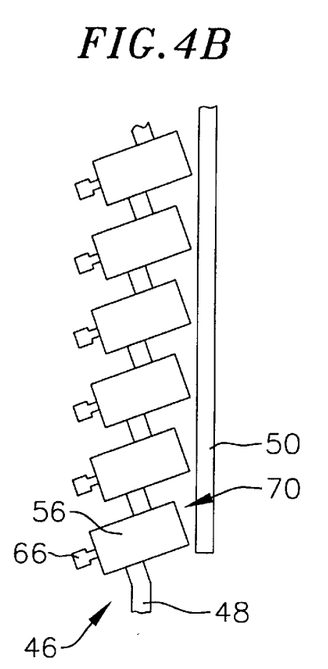
FIG. 4B is a partial plan view showing a greater portion of a scent channel from the exemplary scent storage device illustrated in FIGS. 2 and 3.

The conductors 46 and 50 are preferably formed from relatively low resistance, heat resistant materials such as copper, silver, silver-carbon mixtures, tin and tin alloys and, if necessary, the conductors may be electroless plated with nickel, copper, tin or precious metals such as gold and palladium. The conductor members 54 in the exemplary embodiment are, however, positioned such that there is a space 68 between adjacent conductors and a space 70 between the conductor members and the second conductor 50. Thus, absent other aspects of the scent activation system 40, there would be no electrical connection between the conductors 46 and 50 or between the individual conductor members 54 within conductor 46.

The switching elements 56, which are initially either non-conductive or have a very high resistance, are ultimately used to electrically connect the conductor members 54 to one another, while a series of resistors 72 (note FIG. 4C) are used to electrically connect conductors 46 and 50 to one another. With respect to the switching elements 56, they extend from the first connector portion 58 of one conductor member 54 to the second connector portion 62 of the adjacent conductor member and between the extensions 60 in each connector portion. The resistors 72 extend over the switching elements from the conductor member tabs 66 to the second conductor 50. As illustrated for example in FIGS. 4D and 4E, the scent channels 36 may be sub-divided into a plurality of individual event portions 42 (numbered 42a–42i). The event portions 42 are each composed of the first connector portion 58 from one conductor member 54, the second connector portion 62 of the next conductor member in the series, the switching element 56 connecting first and second connector portions, the resistor 72 connecting the first connector member to the conductor 50, and the portion of the scent material supply 38 positioned over the switching element and resistor.

Figure 4C:
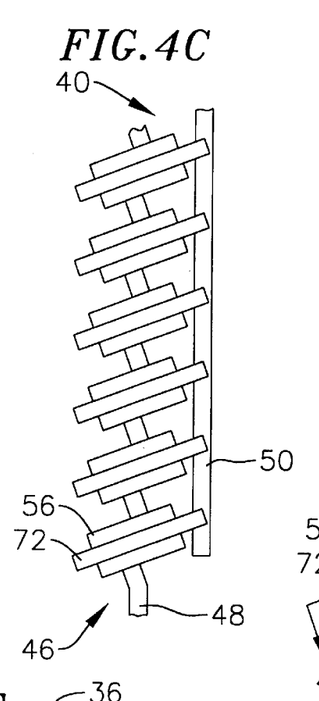
FIG. 4C is a partial plan view showing a still greater portion of a scent channel from the exemplary scent storage device illustrated in FIGS. 2 and 3.
Figure 4D:
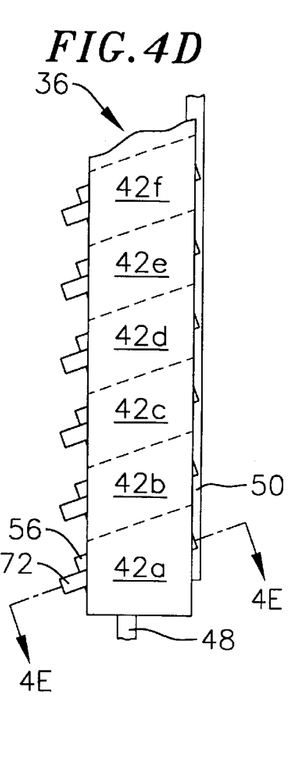
FIG. 4D is a partial plan view showing a completed scent channel from the exemplary scent storage device illustrated in FIGS. 2 and 3.
Figure 4E:
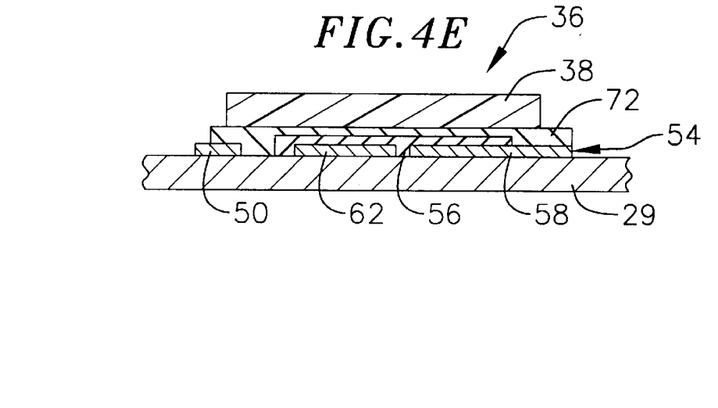
FIG. 4E is a section view taken along line 4E—4E in FIG. 4D.

A scent event in the illustrated embodiment would proceed as follows. During, for example, the first scent invent for a particular scent channel 36, a short power pulse will be transmitted to the first conductor member 54, which is at that time electrically isolated from the next conductor member in the series, by way of the contact 44 and the linear portion 48 of the conductor. The pulse will travel from the conductor member tab 66, through the resistor 72, through the conductor 50 and, finally, through the return line 52 to the contact 53. Passage of the pulse through the resistor 72 causes the resistor to heat up and then vaporize. The vaporization of the resistor should not itself produce any noticeable scent. Materials which will allow the resistors 72 to function in this fashion include carbon and carbon-metal mixtures such as carbon-silver, carbon-nickel and carbon-copper. The heat, in turn, causes the portion of scent material supply 38 associated with event portion 42a to be heated, the wax or other solid material to be vaporized, and the scent material to be released.

The heat from the resistor 72 also causes the switching element 56 to become conductive and electrically connect the first conductor member 54 to the next conductor member in the series. Although other materials with similar properties may be employed, the switching elements in the exemplary embodiment are formed from a fusible material such as solder paste. The flux coating of the solder particles prevents current flow across the solder paste during the power pulse. The flux coating, however, either rises to the surface or is vaporized by the heat as the solder flows together and electrically connects the associated conductor members 54 to one another.

The shape of the exemplary conductor members 54 helps the solder flow in such a manner that adjacent conductor members are connected to one another. More specifically, as the solder liquefies and flows together, the solder bead will have a surface tension that will eventually be equalized over the length of the bead. As the surface tension equalizes, the shape of the connector portions 58 and 62 will cause the solder to wick toward the space 68 between the connector portions. The solder beads will bulge and form a bridge across the space 68, thereby helping to insure that an electrical connection will be made between the connector portions.

It should be noted that the passage of the relatively short power pulse through the resistor 72 must be completed prior to the initiation of the electrical connection between the conductor members 54 in order to insure that only one event portion 42 is consumed per pulse. Thus, the pulse must be long enough to allow the resistor to heat up slowly enough to vaporize the wax or other solid material in the supply 38 and to activate the switching element 56, yet short enough to prevent the consumption of the next event portion 42 in the array. A suitable pulse duration would be 10 milliseconds with a magnitude of 5V, repeated 10 times at a frequency of 5 Hz.

Figure 5:
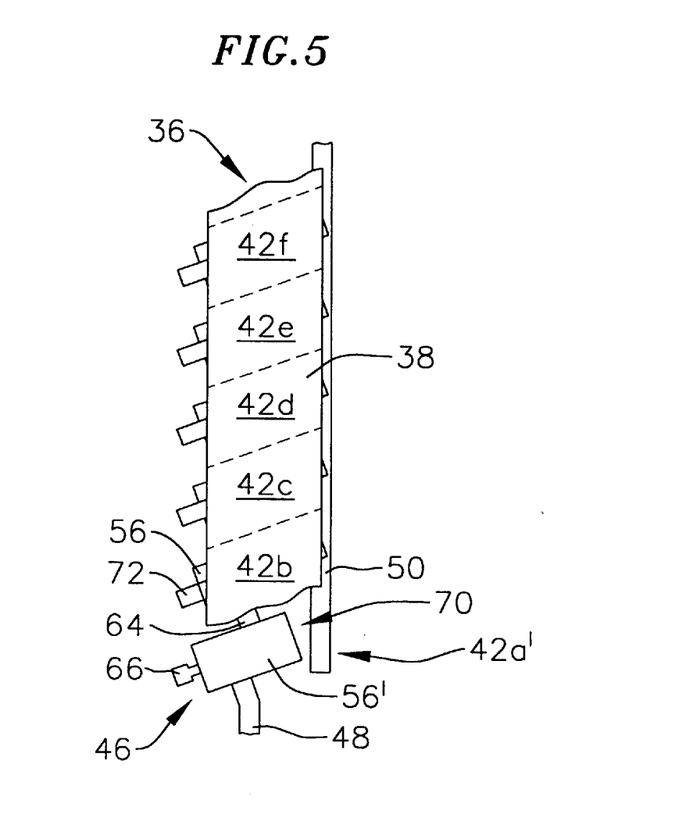
FIG. 5 is a partial plan view showing a scent channel from the exemplary scent storage device illustrated in FIGS. 2 and 3 after one of the scent event portions has been consumed.

The exemplary scent channel 36 subsequent to the consumption of the event portion 42a is illustrated in FIG. 5. The corresponding portion of the scent material supply 38 in the now consumed event portion 42a' is gone. The solid material has been vaporized and the scent material has been disbursed. The resistor 72 is also gone at the fusible area, thereby disconnecting the consumed event portion 42a' from the conductor 50. To that end, the resistor 72 may have a "dog bone" shape to encourage failure at a known point. However, because the switching element 56' is now conductive, the next event portion 42b is electrically connected to the contact 44 and is ready to be consumed in response to the next scent event power pulse.

With respect to manufacturing, one exemplary method of the forming the scent channels 36 and scent activation system 40 is a thick film screen printing process. Referring again to FIGS. 3 and 4A, the first step in the process is to print the contacts 44, individual conductor elements 54 of the conductor 46, the conductor 50, the return line 52 and the contact 53 onto the rear side 32 of the base 29. These elements may also, if desired, be electroless plated with nickel, copper, tin or precious metals such as gold and palladium. Next, as shown in FIG. 4B, the switching elements 56 are printed over the conductor elements 54. The resistors 72 are then printed such that they extend from the conductor member tabs 66, over the switching elements 56, and to the conductors 50 to complete the activation system 40, as illustrated in FIG. 4C. The scent material supply 38 is then printed over the activation system 40 in the manner depicted in FIG. 4D. Finally, if desired, an over-layer of vaporizable unscented material (not shown) may be deposited over the scent channels 36 to prevent the unwanted escape of scents during storage and use.

The thick film printing process also enables the high density formation of the scent channels 36 and scent activation system 40. In a scent storage device such as the exemplary trading card-sized scent storage device 10, which includes nineteen scent channels 36 each having approximately 70 individual event portions, the pitch (or center to center distance) of the channel and the contacts 44 will be about 0.100 inch and the conductor member 54 trace sizes and spaces therebetween are both about 0.015 inch. A 0.100 inch pitch is useful because it is a common connector density and the 0.015 inch trace and space size is within the tolerance of most screening processes.

Figure 6:
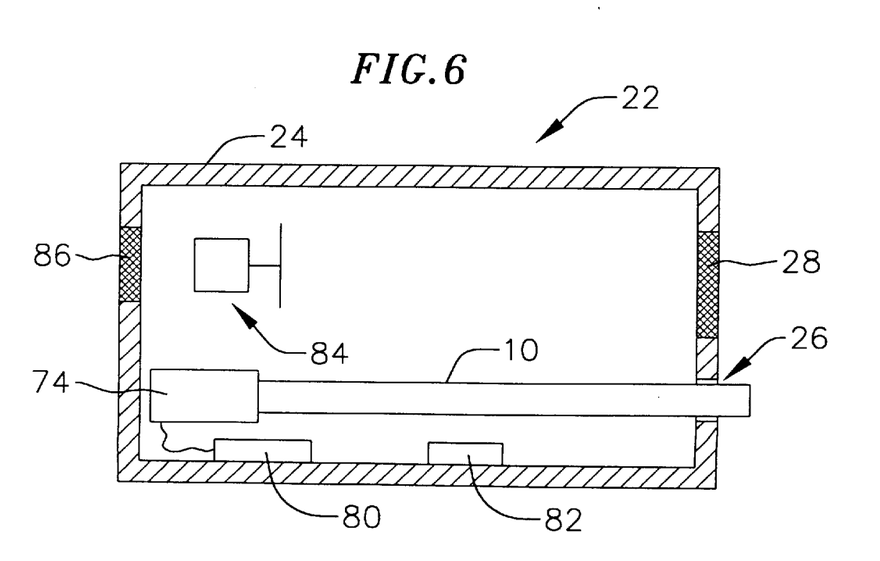
FIG. 6 is partial section view showing the interior of an exemplary scent delivery device.
Figure 7:
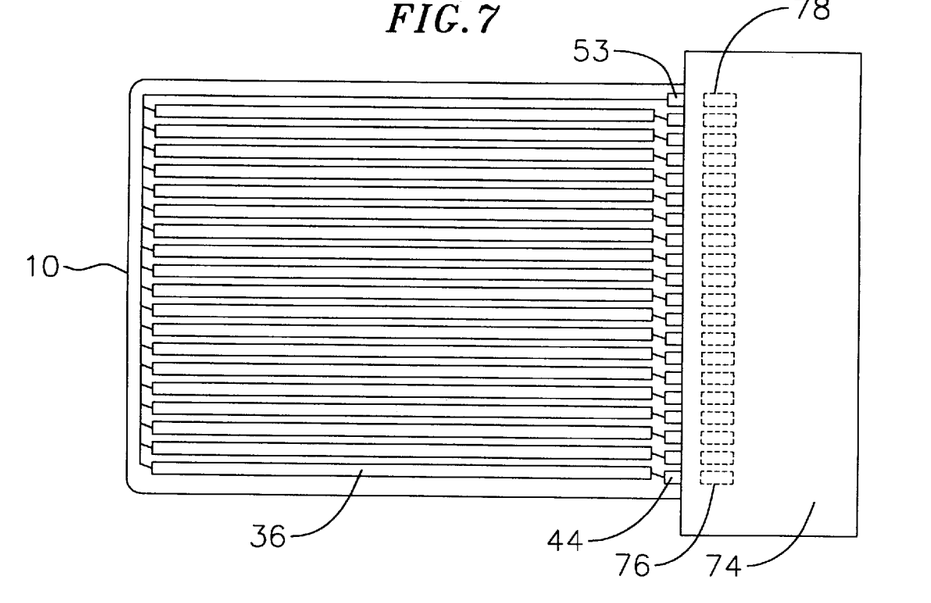
FIG. 7 is a plan view showing an exemplary scent storage device inserted into a connector.

Turning to the scent delivery device, and as illustrated for example in FIGS. 6 and 7, the exemplary scent delivery device 22 includes a connector 74 with a series of pulse contacts 76 that mate with the scent channel contacts 44 on the scent storage device 10 and a contact 78 that mates with the return contact 53. A power supply 80, the operation of which is controlled by a controller 82 and a controller associated with the acoustic/visual stimulator (here, the computer processor 14), is connected to the connector 74. The power supply 80 is provided with a series of capacitors, one for each contact 76, that supply the power pulses in response to signals from the controller 82 to trigger the scent events and then recharge in anticipation of the next scent event signal.

The exemplary scent delivery device 22 may, optionally, also include a motor driven fan 84 that draws air in through a screened inlet 86 and forces it (and the scent material) through the screened outlet 28. The fan 84, which is also controlled controller 82 and the underlying acoustic/visual stimulator, may be run continuously or only activated in response to a scent event depending on the particular application.

Alternatively, a scent delivery device may be provided that does not include a housing into which the entire scent storage device 10 is inserted. Here, the scent storage device 10 would be inserted into a small socket that is adapted to mate with the contacts 76 and 78 and oriented such that the scent channels 36 will face outwardly (and preferably toward the user). No fan would be necessary and the housing would merely house the electronic components described above.

The present passive sequential resistor array has application beyond the scent storage devices. Other exemplary uses include the metering of counters and measured fare applications, such as tickets for buses, ski lifts, amusement parks and other facilities. As illustrated for example in FIG. 8, a ski lift ticket 88 in accordance with a present invention may be constructed as follows. A resistor array that is similar to the scent activation system 40 illustrated in FIG. 4C is mounted on a suitable substrate. A sheet 90 (as opposed to scent material) covers the resistor array as well as the rest of the substrate. The sheet includes a series of numbered elliptical marks 92. Each mark 92, which represents a lift up the mountain, is located over a resistor. Thus, there are ten resistors in the exemplary ski lift ticket 88.

Figure 8:
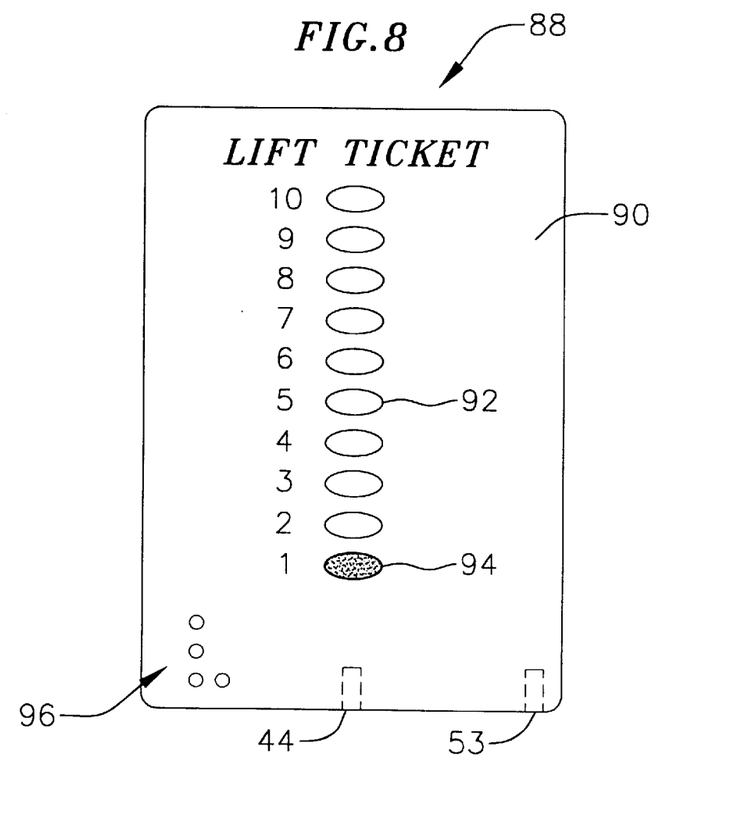
FIG. 8 is a plan view of a ski lift ticket in accordance with a preferred embodiment of a present invention.

Tickets may be "punched" before, during or after the consumer uses the facility by inserting the ticket into a machine that is configured to receive the ticket and supply the requisite energy pulses thereto. When the ticket is "punched" for the first time by applying a pulse to the contact 44 with a device located at the ski lift, the first resistor will burn up. Heat from the resistor will cause the portion of the sheet associated with the resistor (i.e. the first elliptical mark 92) to become discolored. This produces an indicator 94 which shows that the ticket has been used one time, while the yet to be discolored marks 92 indicate that there are nine lifts remaining. The "punching" process will continue until the last mark 92 has been discolored and there are no lifts remaining. At this point, the fact that the ticket is "expired" can be detected electronically, due to the open circuit that remains on the ticket, as well as visually.

The exemplary ticket 88 illustrated in FIG. 8 may also include identification, authentication or security features to prevent counterfeiting and to prevent tickets that are intended for use on one ski lift (or bus line or other place or event) from being used on another. In the embodiment illustrated in FIG. 8, the ticket includes a series of holes 96 in a predetermined pattern and location that can be read by the ticket "punching" device. A ticket without the proper pattern would not be "punched." Alternatively, or in addition, the ticket 88 may include key slots on one or more of the edges. The ticket 88 could also include one or more grounded contacts at a predetermined location for electrical sensing.

Although the present inventions have been described in terms of the preferred embodiments above, numerous modifications and/or additions to the above-described preferred embodiments would be readily apparent to one skilled in the art.

By way of example, but not limitation, the scent material may be a part of the resistors as opposed to a separate structure formed over the passive resistor array. Alternative switching elements may also be employed. One example is a switching element that relies on electrostatic breakdown (as opposed to heat from a resistor). More specifically, a relatively dilute mixture of metal powder (such as copper powder) in a dielectric may be switched from non-conductive to conductive by applying a sufficiently high field. The copper particles have only point contact or are isolated by thin dielectric layers. The field breaks down the dielectric and forms conducting paths. Enough current will then flow to form carbon or melt the copper and heat the scent material supply. In either case, the material becomes quite conductive. Additional information concerning this type of switching element may be found in U.S. Pat. No. 5,006,856.

It is intended that the scope of the present inventions extend to all such modifications and/or additions.

We claim:

1. A ticket, comprising:
   a base member;
   a discolorable member carried by the base member;
   a contact carried by the base member in spaced relation to first and second predetermined portions of the discolorable member; and
   a discoloration system operably connected to the contact and carried by the base member, initially configured such that the discoloration system selectively discolors the first predetermined portion of the discolorable member in response to the application of a first energy pulse to the contact without discoloring the second predetermined portion of the discolorable member, and adapted to be reconfigured by the first energy pulse such that the second predetermined portion of the discolorable member will be discolored in response to the application of a second energy pulse to the contact.

2. A ticket as claimed in claim 1, wherein the base member comprises a relatively small card.

3. A ticket as claimed in claim 1, wherein the base member includes an identification device.

4. A ticket as claimed in claim 3, wherein the identification device comprises a plurality of holes in a predetermined pattern.

5. A ticket as claimed in claim 1, wherein the discolorable member comprises paper.

6. A ticket, comprising:
   a base member;
   a discolorable member carried by the base member and including first and second indicia respectively associated with first and second predetermined portions of the discolorable member; and
   a discoloration system carried by the base member, initially configured such that the discoloration system selectively discolors the first predetermined portion of the discolorable member in response to the application of a first energy pulse without discoloring the second predetermined portion of the discolorable member, and adapted to be reconfigured by the first energy pulse such that the second predetermined portion of the discolorable member will be discolored in response to the application of a second energy pulse.

7. A ticket, comprising:
   a base member;
   a discolorable member carried by the base member; and
   a passive sequential resistor array carried by the base member, initially configured such that the passive sequential resistor array selectively discolors a first predetermined portion of the discolorable member in response to the application of a first energy pulse without discoloring a second predetermined portion of the discolorable member, and adapted to be reconfigured by the first energy pulse such that the second predetermined portion of the discolorable member will be discolored in response to the application of a second energy pulse.

8. A ticket, comprising:
   a base member;
   a discolorable member carried by the base member; and
   a discoloration system, including a series of electrically isolated conductor members, a corresponding series of switches that selectively electrically connect the conductor members, and a corresponding series of resistors respectively associated with the conductor members, carried by the base member, initially configured such that the discoloration system selectively discolors a first predetermined portion of the discolorable member in response to the application of a first energy pulse without discoloring a second predetermined portion of the discolorable member, and adapted to be reconfigured by the first energy pulse such that the second predetermined portion of the discolorable member will be discolored in response to the application of a second energy pulse.

9. A ticket as claimed in claim 8, wherein the switches are formed from a material that is initially substantially non-conductive and that becomes conductive in response to an application of heat from a resistor.

10. A ticket, comprising:
    a base member;
    a discolorable member carried by the base member; and
    a discoloration system located substantially between the base member and the discolorable member, initially configured such that the discoloration system selectively discolors a first predetermined portion of the discolorable member in response to the application of a first energy pulse without discoloring a second predetermined portion of the discolorable member, and adapted to be reconfigured by the first energy pulse such that the second predetermined portion of the discolorable member will be discolored in response to the application of a second energy pulse.

11. A method of metering the use of a facility by a consumer, comprising:
    providing the consumer with a ticket including a base member, a discolorable member carried by the base member, and a discoloration system carried by the base member initially configured such that the discoloration system selectively discolors a first predetermined portion of the discolorable member in response to the application of a first energy pulse without discoloring a second predetermined portion of the discolorable member and adapted to be reconfigured by the first energy pulse such that the second predetermined portion of the discolorable member will be discolored in response to the application of a second energy pulse; and applying one of the first and second energy pulses to the discoloration system after the consumer is provided with the ticket.

12. A method as claimed in claim 11, further comprising the step of:

reviewing the ticket to determine whether the first and second predetermined portions have been discolored.

13. A method as claimed in claim 11, wherein the applied energy pulse comprises the first energy pulse, the method further comprising the step of:

applying the second energy pulse to the discoloration system when the user uses the facility.

14. A method as claimed in claim 11, further comprising the step of:

determining whether the ticket is authentic.

15. A method as claimed in claim 11, wherein the step of applying one of the first and second energy pulses to the discoloration system comprises applying one of the first and second energy pulses to the discoloration system prior to the consumer using the facility.

16. A method as claimed in claim 11, wherein the step of applying one of the first and second energy pulses to the discoloration system comprises applying one of the first and second energy pulses to the discoloration system after the consumer uses the facility.

17. A method as claimed in claim 11, further comprising the step of:

returning the ticket to the consumer after applying one of the first and second energy pulses to the discoloration system.

18. A method of metering the use of a facility by a consumer, comprising:

providing the consumer with a ticket having first and second indicia;

discoloring a first predetermined portion of the ticket associated with the first indicia after the consumer has been provided with the ticket by applying a first energy pulse to the ticket without discoloring a second predetermined portion of the ticket associated with the second indicia; and allowing the user to use the facility.

19. A method as claimed in claim 18, further comprising the step of:

discoloring a second predetermined portion of the ticket by applying a second energy pulse.

20. A method as claimed in claim 18, further comprising the step of:

reviewing the ticket to determine whether the first and second predetermined portions have been discolored.

21. A method as claimed in claim 18, further comprising the step of:

determining whether the ticket is authentic.

22. A method as claimed in claim 18, wherein the step of discoloring a first predetermined portion of the ticket comprises discoloring a first predetermined portion of the ticket prior to the consumer using the facility.

23. A method as claimed in claim 18, wherein the step of discoloring a first predetermined portion of the ticket comprises discoloring a first predetermined portion of the ticket subsequent to the consumer using the facility.

24. A method as claimed in claim 18, wherein the step of discoloring a first predetermined portion of the ticket comprises discoloring a first predetermined portion of the ticket after the consumer has been provided with the ticket by applying a first electrical energy pulse.

25. A method as claimed in claim 18, wherein the ticket includes an electrical contact and the step of discoloring a first predetermined portion of the ticket comprises discoloring a first predetermined portion of the ticket after the consumer has been provided with the ticket by applying a first electrical energy pulse to the electrical contact.

26. A method of metering the use of a facility by a consumer, comprising:

providing the consumer with a ticket;

discoloring a first predetermined portion of the ticket by inserting the ticket into a punching device and applying a first energy pulse to the ticket with the punching device without discoloring a second predetermined portion of the ticket; and allowing the user to use the facility.

27. A method of metering the use of a facility by a consumer, comprising:

providing the consumer with a ticket including a base member, a discolorable member carried by the base member, and a discoloration system carried by the base member initially configured such that the discoloration system selectively discolors a first predetermined portion of the discolorable member in response to the application of a first energy pulse without discoloring a second predetermined portion of the discolorable member and adapted to be reconfigured by the first energy pulse such that the second predetermined portion of the discolorable member will be discolored in response to the application of a second energy pulse; and inserting the ticket into a punching device and applying one of the first and second energy pulses to the discoloration system with the punching device when the consumer uses the facility.

28. A ticket, comprising:

a base member;

a discolorable member carried by the base member; and a discoloration system carried by the base member, initially configured such that the discoloration system selectively discolors a first predetermined portion of the discolorable member in response to the application of a first electrical energy pulse to the discoloration system without discoloring a second predetermined portion of the discolorable member, and adapted to be reconfigured by the first electrical energy pulse such that the second predetermined portion of the discolorable member will be discolored in response to the application of a second electrical energy pulse to the discoloration system.

29. A ticket as claimed in claim 28, wherein the discolorable member comprises paper.

30. A ticket as claimed in claim 28, wherein the discolorable member includes first and second indicia respectively associated with the first and second predetermined portions of the discolorable member.

31. A ticket as claimed in claim 28, wherein the discoloration system comprises a passive sequential resistor array.

32. A ticket as claimed in claim 28, further comprising:

an electrical contact operably connected to the discoloration system.

33. A method of metering the use of a facility by a consumer, comprising:

providing the consumer with a ticket including a base member, a discolorable member carried by the base member, and a discoloration system carried by the base member initially configured such that the discoloration system selectively discolors a first predetermined portion of the discolorable member in response to the application of a first electrical energy pulse without discoloring a second predetermined portion of the discolorable member and adapted to be reconfigured by the first electrical energy pulse such that the second predetermined portion of the discolorable member will be discolored in response to the application of a second electrical energy pulse; and applying one of the first and second electrical energy pulses to the discoloration system when the consumer uses the facility.

34. A method as claimed in claim 33, wherein the ticket includes an electrical contact that is operable connected to the discoloration system and the step of applying one of the first and second electrical energy pulses to the discoloration system comprises applying one of the first and second electrical energy pulses to the electrical contact.

35. A method as claimed in claim 33, wherein the step of applying one of the first and second electrical energy pulses to the discoloration system comprises applying one of the first and second electrical energy pulses to the discoloration system prior to the consumer using the facility.

* * * * *